(12) United States Patent
Nikolovski

(10) Patent No.: US 9,417,217 B2
(45) Date of Patent: Aug. 16, 2016

(54) SYSTEM FOR DETECTING AND LOCATING A DISTURBANCE IN A MEDIUM AND CORRESPONDING METHOD

(75) Inventor: Jean-Pierre Nikolovski, Chatenay-Malabry (FR)

(73) Assignee: Commissariat a l'energie atomique et aux energies alternatives, Paris (FR)

( * ) Notice: Subject to any disclaimer, the term of this patent is extended or adjusted under 35 U.S.C. 154(b) by 414 days.

(21) Appl. No.: 13/988,222

(22) PCT Filed: Oct. 27, 2011

(86) PCT No.: PCT/FR2011/052523
§ 371 (c)(1),
(2), (4) Date: May 17, 2013

(87) PCT Pub. No.: WO2012/069722
PCT Pub. Date: May 31, 2012

(65) Prior Publication Data
US 2013/0233080 A1   Sep. 12, 2013

(30) Foreign Application Priority Data
Nov. 23, 2010   (FR) ...................................... 10 59657

(51) Int. Cl.
*G01N 29/34* (2006.01)
*G01S 7/521* (2006.01)
(Continued)

(52) U.S. Cl.
CPC .............. *G01N 29/346* (2013.01); *G01S 7/521* (2013.01); *G01S 15/876* (2013.01); *G06F 3/0436* (2013.01)

(58) Field of Classification Search
CPC ...... H01L 41/09; G01N 29/346; G06F 3/043; G06F 3/0433; G06F 3/0436; G01S 15/876; G01S 7/521

USPC ..................... 73/628, 629; 345/173, 177, 178
See application file for complete search history.

(56) References Cited

U.S. PATENT DOCUMENTS

2002/0075243 A1* 6/2002 Newton ................ G06F 3/0421
345/173
2003/0025721 A1* 2/2003 Clapper .................. G06F 3/014
715/700

(Continued)

FOREIGN PATENT DOCUMENTS

FR   2 916 545   11/2008

OTHER PUBLICATIONS

Liu, Y. et al. "Acoustic Wave Approach for Multi-Touch Tactile Sensing", Micro-Nanomechatronics and Human Science, 2009, MHS 2009. International Symposium on IEEE, pp. 574-579, (Nov. 9, 2009), XP031579245.

(Continued)

*Primary Examiner* — Laura Martin
*Assistant Examiner* — Suman K Nath
(74) *Attorney, Agent, or Firm* — Oblon, McClelland, Maier & Neustadt, L.L.P.

(57) ABSTRACT

A system including a mechanism emitting successive acoustic waves in a medium, a mechanism receiving the successive acoustic waves after propagation thereof in the medium, configured to supply a reception signal based on the successive acoustic waves received, and a mechanism detecting and locating disturbance in the medium on the basis of the reception signal. The emitting mechanism is configured such that, amplitude and/or phase spectrum of each acoustic wave having, at a specific frequency at least, an amplitude, or phase, varying in the medium according to a specific spatial distribution of the amplitude, or phase, and the spatial distributions of the amplitude, or phase, of the successive acoustic waves are mutually different.

12 Claims, 8 Drawing Sheets

Figure 1:
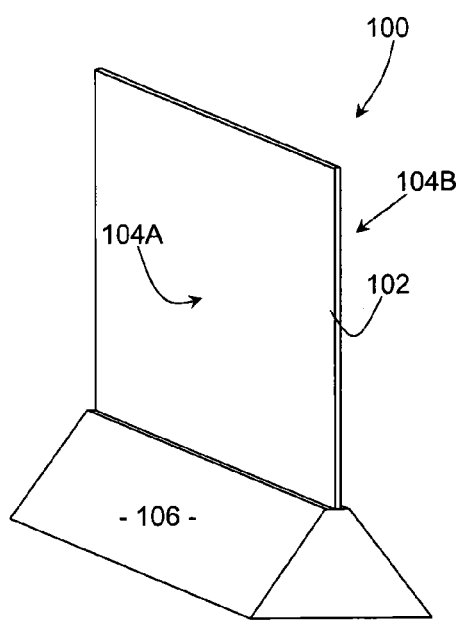

(51) Int. Cl.
  *G01S 15/87* (2006.01)
  *G06F 3/043* (2006.01)

(56) References Cited

U.S. PATENT DOCUMENTS

| | | | | |
|---|---|---|---|---|
| 2007/0176907 | A1* | 8/2007 | Ishii | G06F 3/0436 345/177 |
| 2008/0316184 | A1* | 12/2008 | D'Souza | G06F 3/0418 345/173 |
| 2009/0273583 | A1* | 11/2009 | Norhammar | G06F 3/0436 345/177 |
| 2010/0283745 | A1* | 11/2010 | Nikolovski | G06F 3/0436 345/173 |

OTHER PUBLICATIONS

Ing, R.K. et al. "Tactile Touch Plate with Variable Boundary Conditons", The Journal of the Acoustical Society of America, vol. 123, No. 5, pp. 4225-4229, (Jan. 1, 2008), XP055002822.
International Search Report Issued Jun. 21, 2012 in PCT/FR11/52523, Filed Oct. 27, 2011.
U.S. Appl. No. 14/235,702, filed Jan. 28, 2014, Nikolovski, et al.

* cited by examiner $k = 0$ ... $k = 0.2$ $k = 0.5$ ... $k = 0.8$ ... $k = 1$ $\varphi = 0$ $\varphi = \pi/2$

SYSTEM FOR DETECTING AND LOCATING A DISTURBANCE IN A MEDIUM AND CORRESPONDING METHOD

The present invention relates to a system for detecting and locating a disturbance in a medium and a corresponding method and computer program.

Various systems for detecting and locating a disturbance in a medium are known in the prior art, comprising means for emitting successive acoustic waves in the medium, means for receiving successive acoustic waves after the propagation thereof in the medium, designed to supply a reception signal on the basis of the successive acoustic waves received and means for detecting and locating the disturbance in the medium on the basis of the reception signal.

U.S. Pat. No. 6,741,237 B1 describes a system using the disturbance of a transit time of seismic acoustic waves propagated in an object between an emitting transducer and at least two receiving transducers arranged about the object such that the disturbance induced by touch gives rise to different transit time fluctuations from the touch area to the two receiving transducers. This system is solely based on differences in transit times and requires the arrangement of the transducers at precise locations about the object to maximise the transit time differentials in at least two separate directions, for example in the corners for a rectangular plate.

The patent FR 07 03651 describes a system using relative absorption signature recognition of a seismic acoustic wave, on a set of resonance figures of the interface object. The relative damping and phase-shift for each frequency induced by touch are one of the components of a relative damping vector constructed on a predefined number of resonance figures. Nevertheless, this system involves the drawback of arranging the sensors at locations of the object suitable for breaking up the axes of symmetry of the object so as to obtain satisfactory reliability in respect of location. Moreover, the resonance figures can easily be disturbed by the conditions for mounting the interface in the supporting member thereof, particularly if the plate can slide in a track, i.e. if the conditions at the limits are not fixed.

U.S. Pat. No. 6,396,484 B1 describes a system using the measurement of surface seismic acoustic wave transit times, damped by finger contact. This system is characterised by a precise path to be followed by an acoustic wave in a known time interval and at a fixed frequency, typically of a few megahertz. The position of the touch is correlated with an attenuation of the signal at a specific time dependent on the path followed by the wave determined by partial reflectors arranged in perpendicular directions on the edges of a rectangular plate. This system involves the drawback of requiring physical etching of the object so as to give rise to an array of partial reflectors of the surface wave travelling through the object. The paths followed by the wave are thus fixed and known.

It may thus be sought to envisage a system for detecting and locating a disturbance in a medium suitable for doing away with at least some of the abovementioned problems and constraints.

The invention thus relates to a system for detecting and locating a disturbance in a medium, comprising:
  means for emitting successive acoustic waves in the medium,
  means for receiving the successive acoustic waves after the propagation thereof in the medium, designed to supply a reception signal based on the successive acoustic waves received, and
  means for detecting and locating the disturbance in the medium on the basis of the reception signal,
the emitting means being designed such that, the amplitude and/or phase spectrum of each acoustic wave having, at a specific frequency at least, an amplitude, or phase, varying in the medium according to a specific spatial distribution of the amplitude, or phase, these spatial distributions of the amplitude, or phase, of the successive acoustic waves are mutually different.

By means of the present invention, the disturbance of the medium gives rise to acoustic waves successively received by the reception device and thus a variation of the reception signal. However, this variation is dependent on the spatial distribution of the amplitude or phase of the acoustic waves. As the emitting means emit acoustic waves successively having different spatial distributions, the system according to the invention makes it possible to obtain, for the same disturbance, a plurality of successive variations (one per spatial distribution) in the reception signal. Each of these variations is one characteristic of the disturbance. With sufficient characteristics, i.e. sufficient different spatial distributions, it is possible to detect and locate this disturbance.

In this way, it is no longer necessary to envisage acoustic wave guides or to use transit time calculations.

Optionally, the emitting means comprise:
  an emitting device comprising first and second acoustic wave sources respectively having first and second radiation patterns, which are concentric and different to each other,
  means for modifying the relative weighting of the amplitudes of the acoustic waves of the first and second sources, the successive weightings corresponding to the successive spatial distributions, respectively.

Also optionally, each radiation pattern has an axis in the direction whereof it is zero, the axes forming an angle different to zero together.

Also optionally:
  each acoustic wave source comprises two piezoelectric transducing elements,
  the emitting means comprise means for polarising the two piezoelectric transducing elements having two mutually opposite potentials, respectively.

Also optionally, the emitting device comprises a piezoelectric element coupled with the medium and four electrodes covering a respective quarter of one face of the piezoelectric element, the two transducing elements of the first source comprising two mutually opposite electrodes, respectively, and the two transducing elements of the second source comprising the two other mutually opposite electrodes, respectively.

Also optionally:
  the medium comprises a plate having a contact surface,
  the acoustic waves are seismic acoustic waves propagated in the plate,
  the disturbance is a contact on the contact surface.

Also optionally:
  the medium comprises a fluid on the surface of a plate,
  the acoustic waves are compression acoustic waves propagated in the fluid on the plate surface,
  the disturbance is the presence of an interruption in impedance on the plate surface, for example caused by the presence of an obstacle.

Also optionally, the piezoelectric element comprises a sleeve for emitting the compression acoustic waves.

The invention also relates to a method for detecting and locating a disturbance in a medium, comprising:
- supplying control signals to a device for emitting acoustic waves, so that the emitting device emits successive acoustic waves in the medium,
- receiving a reception signal from a device for receiving acoustic waves receiving successive acoustic waves after the propagation thereof in the medium,
- detecting and locating the disturbance in the medium on the basis of the reception signal, characterised in that:
- the control signals are designed such that, the amplitude and/or phase spectrum of each acoustic wave having, at a specific frequency at least, an amplitude, or phase, varying in the medium according to a specific spatial distribution of the amplitude, or phase, these spatial distributions of the amplitude, or phase, of the successive acoustic waves are mutually different.

Optionally,
- the control signals are supplied intermittently such that the mean exposure output, even in the ultrasonic range, remains below 85 dB, with a reference of $2 \cdot 10^{-5}$ Pa, in the air one centimeter from the device for emitting acoustic waves,
- the control signals having a specific excitation frequency band, and the method further comprises, before detecting and locating the disturbance in the medium on the basis of the reception signal:
- amplifying the reception signal and converting same by means of an analogue-digital converter, the amplification being configured such that the amplitude of the received signal in the absence of disturbance reaches the full quantification scale of the analogue-digital converter,
- performing band-pass filtering of the reception signal, on a frequency band corresponding to the excitation frequency band.

Finally, the invention also relates to a downloadable computer program from a communication network and/or saved on a computer-readable medium and/or executable by a processor, characterised in that it comprises instructions for executing steps of a method for detecting and locating a disturbance in a medium according to the invention, when said program is executed on a computer.

Figure 2:
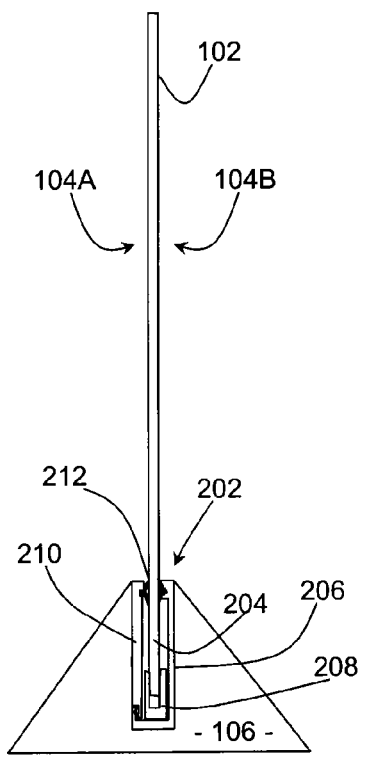
Figure 3:
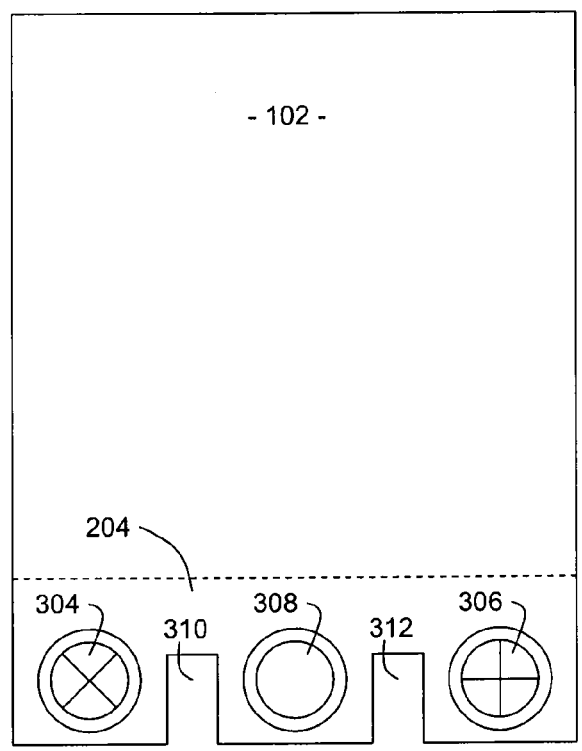
Figure 4:
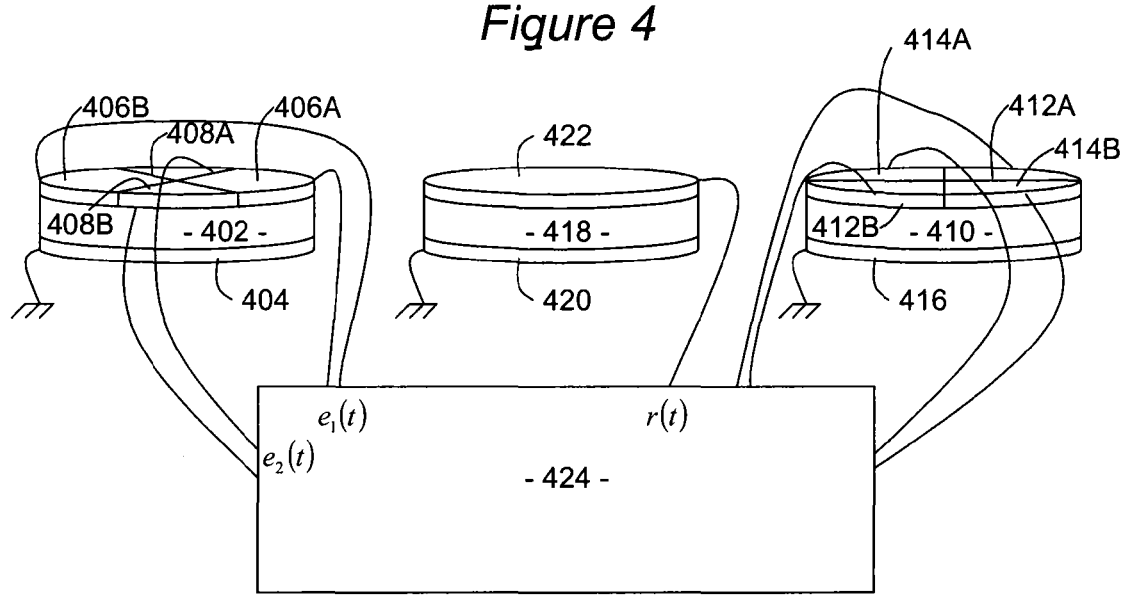
Figure 5:
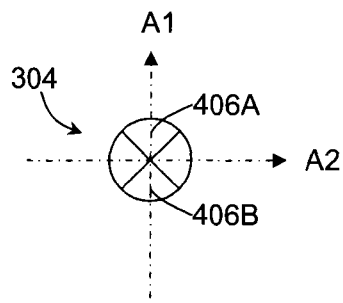
Figure 6:
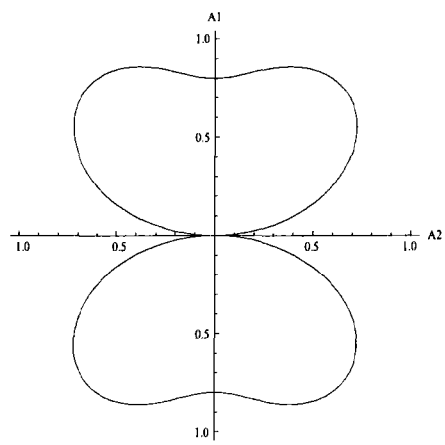
Figure 8:
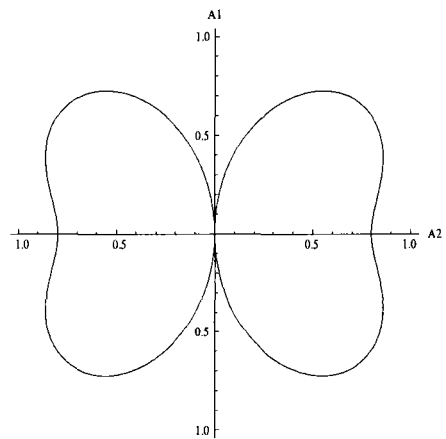
Figure 7:
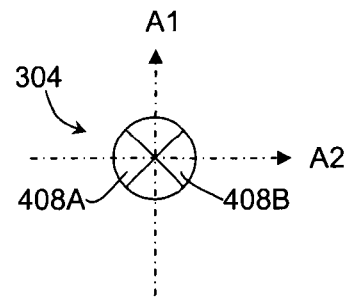
Figure 9:
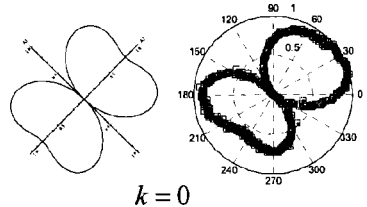
Figure 10:
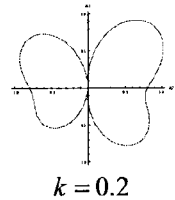
Figure 11:
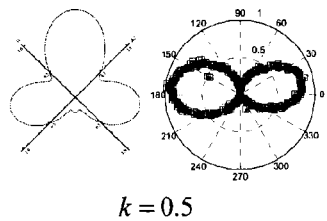
Figure 12:
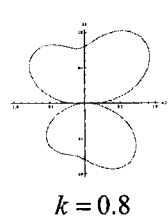
Figure 13:
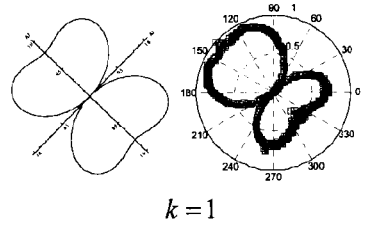
Figure 14:
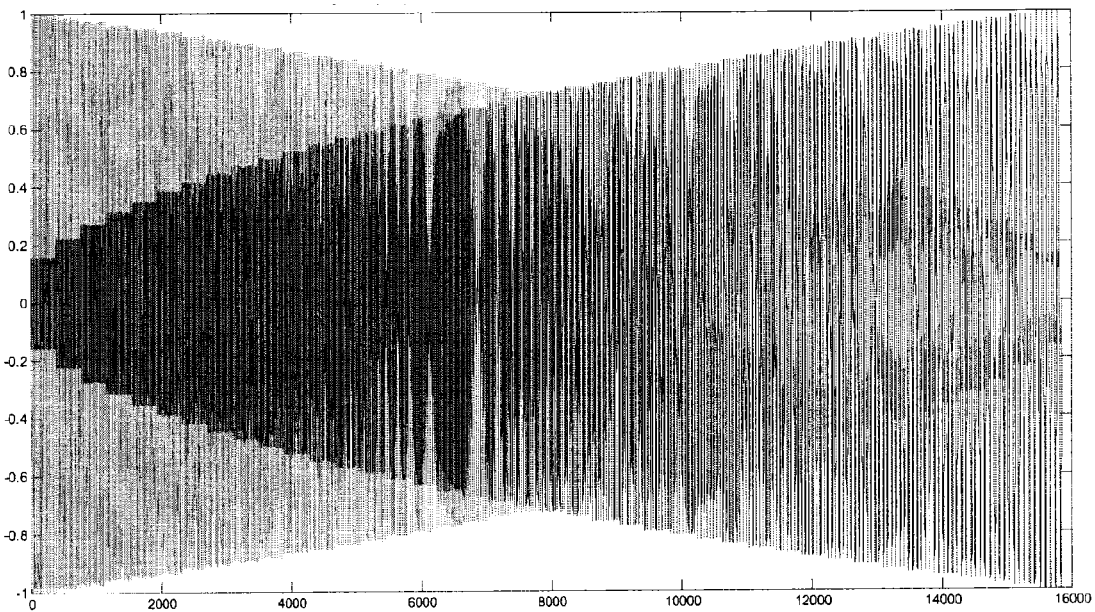
Figure 15:
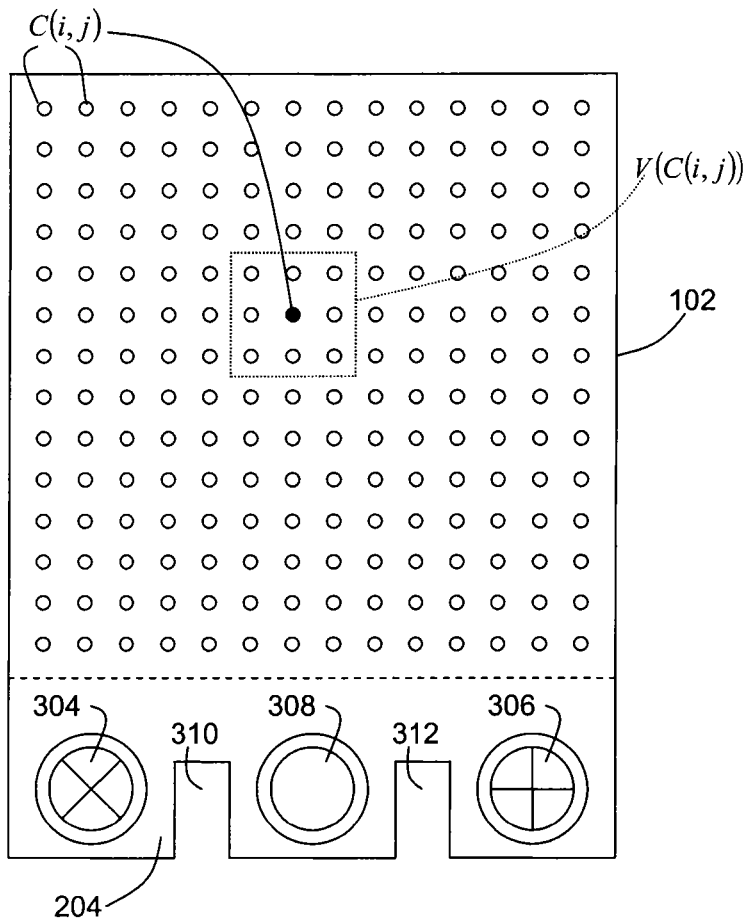
Figure 16:
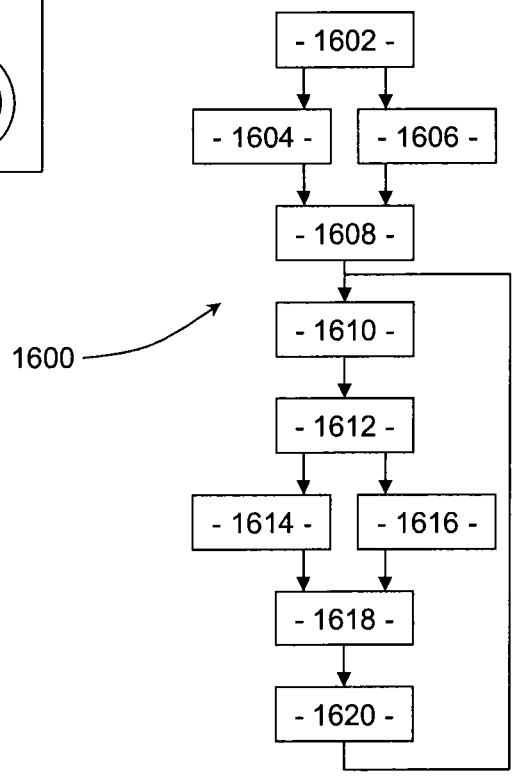
Figure 17:
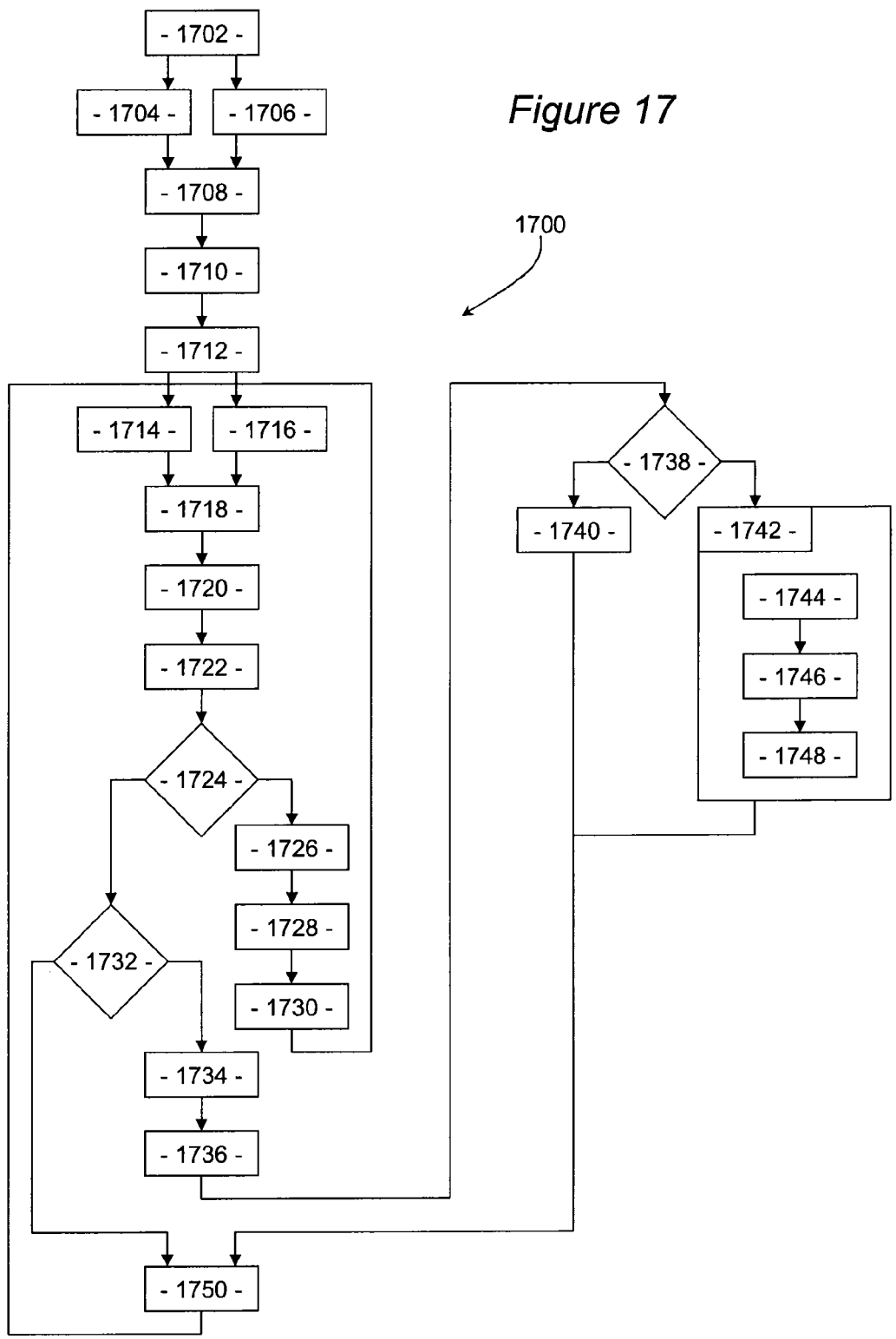
Figure 18:
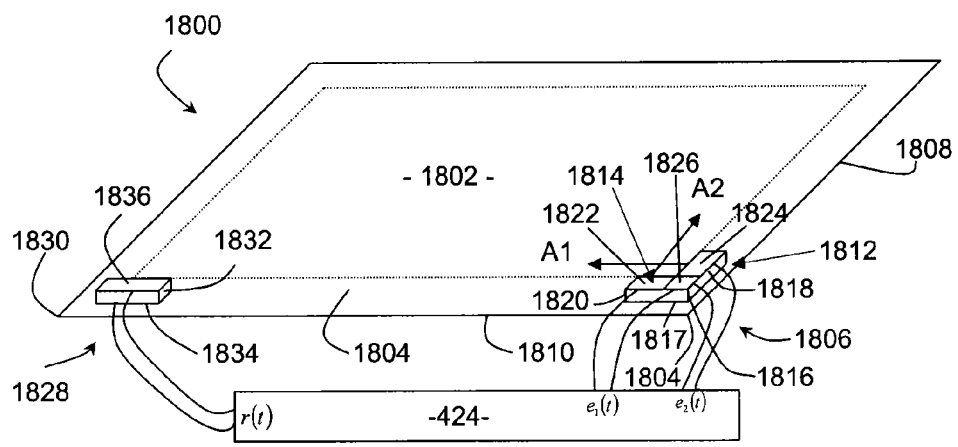
Figure 19:
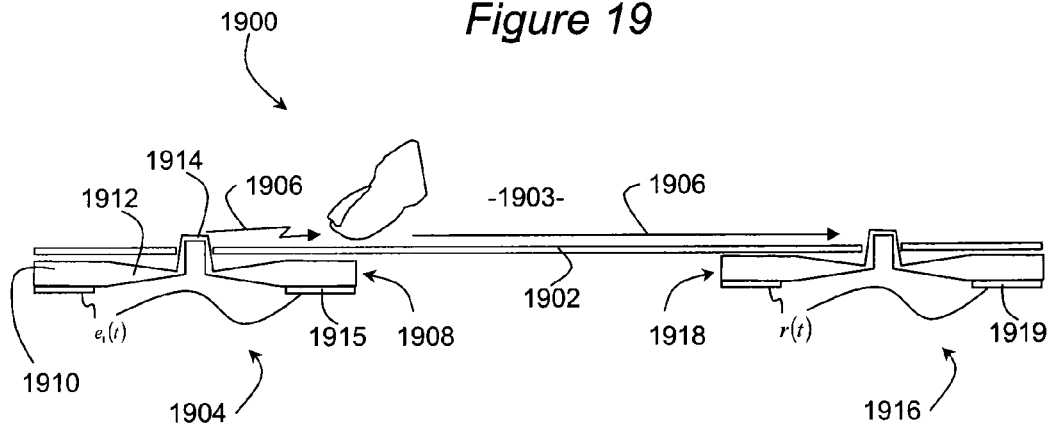
Figure 20:
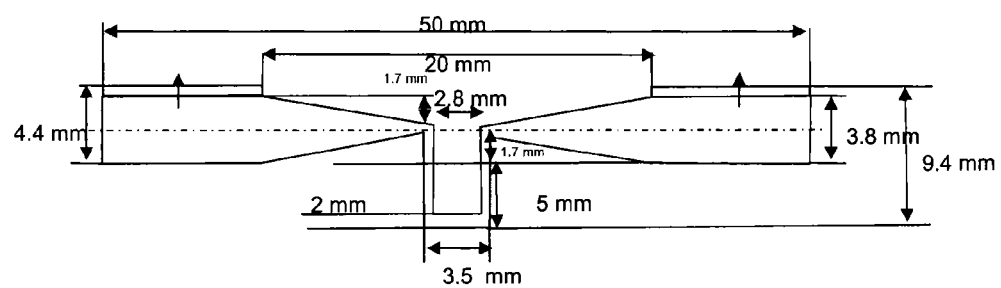
Figure 21:
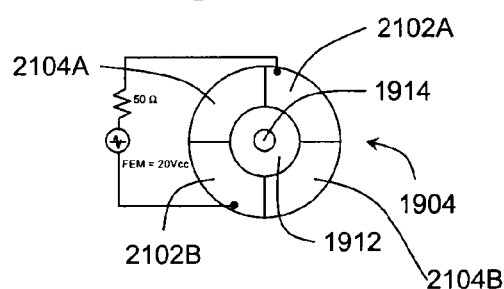
Figure 22:
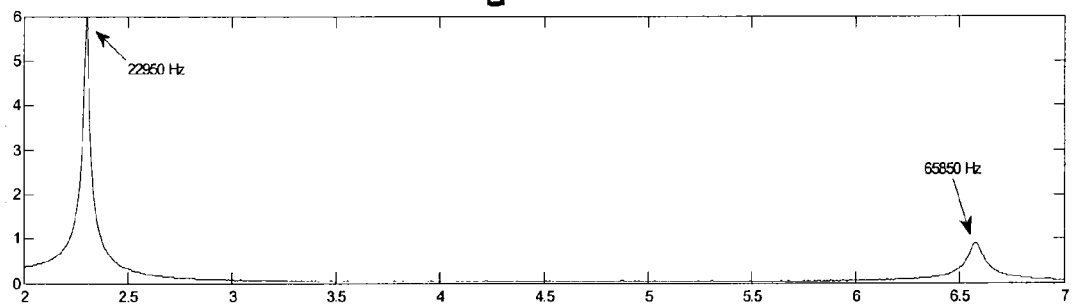
Figure 23:
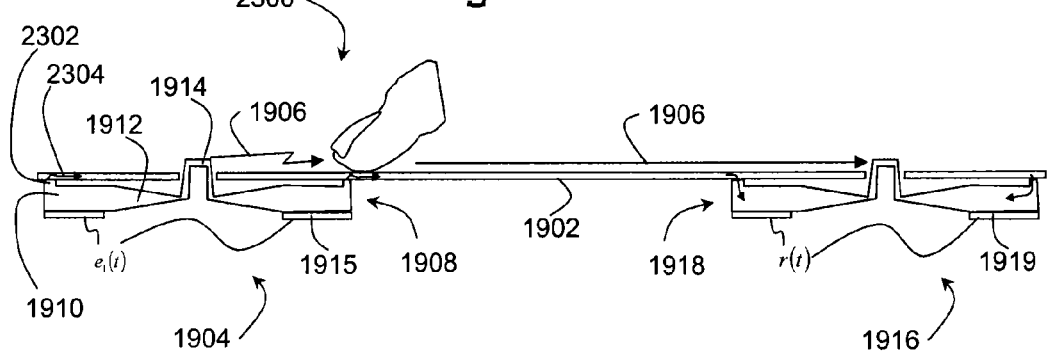
Figure 24:
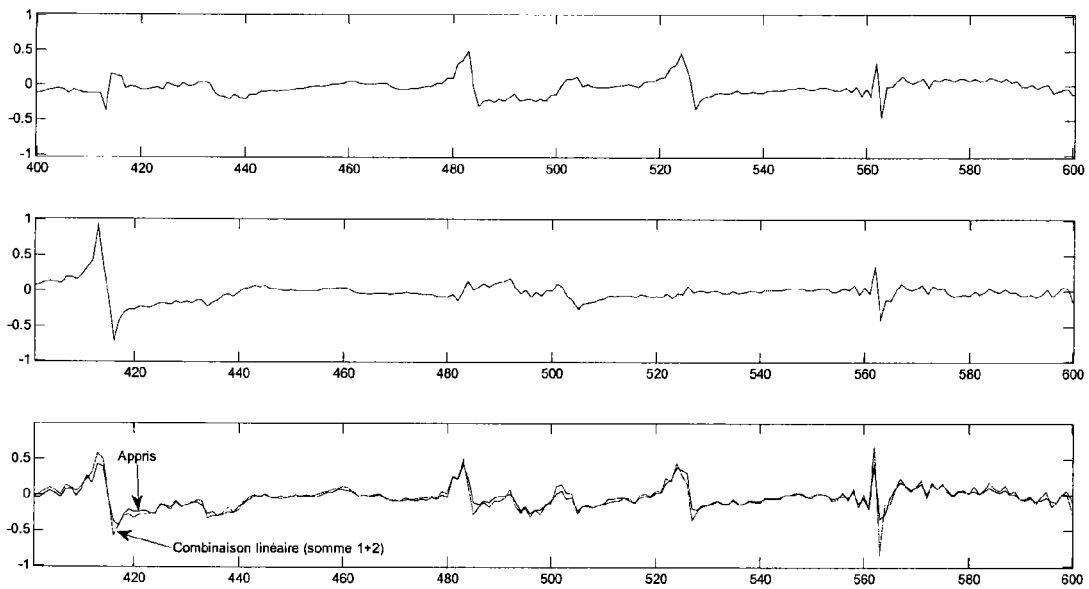
Figure 25:
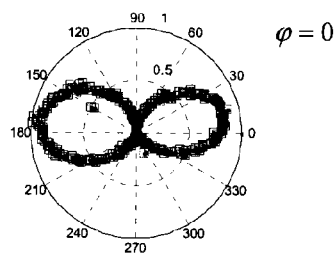
Figure 26:
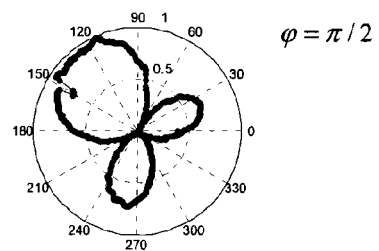
Figure 27:
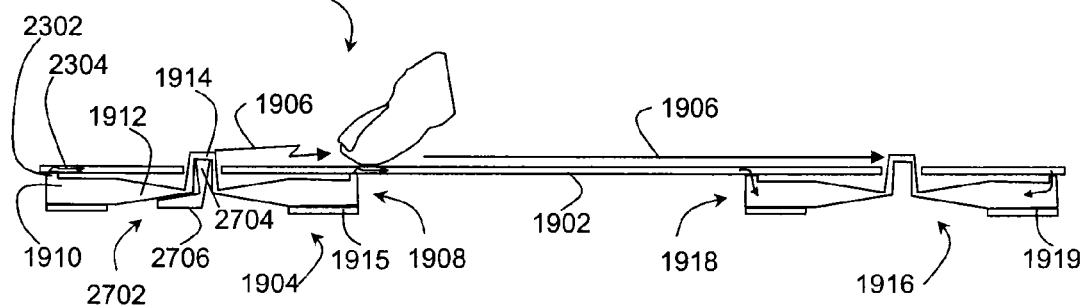

The invention will be understood more clearly using the description hereinafter, given merely as an example, with reference to the appended figures wherein:

FIG. 1 is a three-dimensional view of a first touch surface system implementing the invention, FIG. 2 is a sectional view of the touch surface system in FIG. 1, FIG. 3 is a front view of a glass plate of the system in FIG. 1, FIG. 4 is a diagram representing devices for emitting and receiving acoustic waves and a computer system device of the touch surface system in FIG. 1, FIG. 5 is a top view of the emitting device in FIG. 4, wherein a first acoustic wave source is shown, FIG. 6 is a directivity pattern of the first acoustic wave source in FIG. 5, FIG. 7 is a top view of the emitting device in FIG. 4, wherein a second acoustic wave source is shown, FIG. 8 is a directivity pattern of the source acoustic wave source in FIG. 7, FIGS. 9 to 13 are theoretical and experimental directivity patterns of the emitting device in FIG. 4 according to various relative contributions of both sources, FIG. 14 is a graph illustrating two control signals supplied by the computer system device to the two sources of the emitting device in FIG. 4 respectively, FIG. 15 is a front view of the glass plate in FIG. 3, wherein reference contacts are shown, FIG. 16 is a block diagram of a training method, FIG. 17 is a block diagram of a monitoring method, FIG. 18 is a three-dimensional view of a second touch surface system implementing the invention, FIG. 19 is a sectional view of a contactless interface system implementing the invention, FIG. 20 is a sectional view of a resonating disk of the system in FIG. 19, FIG. 21 is a top view of the resonating disk in FIG. 20, FIG. 22 is a curve showing the vibration amplitude of a sleeve perpendicular to the axis of symmetry thereof, when the resonating disk in FIGS. 20 and 21 is actuated, FIG. 23 is a sectional view of an interface system with and without contact implementing the invention, FIG. 24 is a set of three curves showing the principle of detection of a plurality of simultaneous disturbances, FIGS. 25 and 26 represent directivity patterns of the emitting device in FIG. 4 according to various phase shifts between the two sources, and FIG. 27 represents a sectional view of an enhancement of the interface system in FIG. 23.

With reference to FIG. 1, a touch surface system 100 according to an example of an embodiment of the invention firstly comprises a glass plate 102 having two opposite faces 104A, 104B.

The glass plate 102 may have dimensions of up to 1.8 meters high, 0.7 meters wide and 8 millimeters thick. It may be made of monolithic, tempered or laminated glass, for example type 442, i.e. four millimeters of glass, two millimeters of PVB (PolyVinyl Butyral) intermediate coating and a further four millimeters of glass.

The touch surface system 100 further comprises a base 106 for holding the glass plate 102 in a vertical position. The glass plate 102 is inserted into the base 106 by means of a bottom edge, whereas the three other edges may remain bare.

With reference to FIG. 2, the base 106 defines a slot 202 wherein a bottom portion 204 of the glass plate 102 is inserted and secured by a frame 206, wedges 208 and a stop 210. A packing seal 212 ensures tightness at the opening of the slot 202.

With reference to FIG. 3, the touch surface system 100 further comprises two devices 304, 306 for emitting seismic acoustic waves in the plate 102 and one device 308 for receiving seismic acoustic waves, the three devices being secured, for example by bonding, in the inner portion 204 of the glass plate 102.

Preferably, the three devices 304, 306, 308 are aligned along the bottom edge of the glass plate 102.

Moreover, in order to do away with any ambiguity in respect of contact location, the receiving device 308 is preferably situated between the two emitting devices 304, 306. However, it is also possible to arrange the two emitting devices 304, 306 on the same side of the receiving device 308.

Moreover, the emitting devices 304, 306 are preferably arranged at the ends of the bottom edge of the glass plate 102.

Two notches 310, 312 are provided in the bottom edge, the notches extending between the receiving device 308 and each emitting device 304, 306, respectively, so as to limit the direct coupling between each emitting device 304, 306 and the receiving device 308. Preferably, the notches 310, 312 do not extend beyond the emitting 304, 306 and receiving 308 devices.

The emitting 304, 306 and receiving 308 devices may be attached on either side of the glass plate 102.

Preferably, the emitted and received acoustic waves are bending waves having a large wavelength with respect to the thickness of the glass plate 102. They are bulk waves. The energy of the acoustic field of these waves is distributed throughout the thickness of the glass plate 102.

If the glass plate 102 is homogeneous and isotropic, the system 100 is preferably designed to detect contacts on the two contact surfaces 104A, 104B, independently of the contact surface 104A or 104B where the emitting 304, 306 and receiving 308 devices are attached.

With reference to FIG. 4, the first emitting device 304 comprises a piezoelectric disk 402 (i.e. made of piezoelectric material) having a bottom face covered by a lower electrode 404 whereby the first emitting device 304 is pressed against the glass plate 102. The piezoelectric disk 402 further has a top face covered with four upper electrodes 406A, 406B and 408A, 408B, each covering a respective quarter of the top face. In the example described, the piezoelectric disk 402 is polarised uniformly on the entire surface thereof.

The second emitting device 306 is identical to the first emitting device and as such comprises a piezoelectric disk 410 equipped with four upper electrodes 412A, 412B and 414A, 414B on the top face thereof and a lower electrode 416 on the bottom face thereof.

The receiving device 308 comprises a piezoelectric disk 418 having a bottom face covered by a lower electrode 420 pressing against the glass plate 102. It further comprises a top face covered with an upper electrode 422.

The touch surface system 100 further comprises a computer system device 424 connected to the electrodes of the emitting 304, 306 and receiving 308 devices.

More specifically, the lower electrodes 404, 416, 420 of the two emitting devices 304, 306 and the receiving device 308 are connected to a ground of the computer system device 424. Moreover, the computer system device 424 is designed to supply the following control signals to the first emitting device: $e_1(t)$ between the two opposite electrodes 406A, 406B, and $e_2(t)$ between the two other opposite electrodes 408A, 408B. In the example described, the two opposite electrodes are polarised between two mutually opposite potentials, respectively:

$$-\frac{e_1(t)}{2} \text{ and } +\frac{e_1(t)}{2},$$

and the two other opposite electrodes between two mutually opposite potentials, respectively:

$$-\frac{e_2(t)}{2} \text{ and } +\frac{e_2(t)}{2}.$$

The upper electrode 422 of the receiving device 308 is connected to the computer system device 424 to supply a reception signal r(t), on the basis of the acoustic waves received by the receiving device 308.

The computer system device 424 is also designed to supply control signals to the second emitting device 306, as for the first emitting device 304, as such, they will not be described hereinafter.

The computer system device 424 is designed to detect and locate a contact on any of the contact surfaces 104A, 104B on the basis of the reception signal r(t) corresponding to the seismic acoustic waves received, i.e. the seismic acoustic waves emitted by the first and second emitting devices 304, 306 and propagated in the glass plate 102.

For this purpose, the computer system device 424 is designed to implement the actions detailed with reference to FIGS. 16 and 17.

For example, the computer system device 424 comprises a processing unit (not shown) for executing instructions of a computer program (not shown) in order to implement these actions.

Alternatively, the computer system device 424 could be replaced by an electronic device consisting solely of electronic circuits (with no computer program) for implementing the same actions.

The terms radiation and directivity patterns will be used hereinafter.

A radiation pattern of an acoustic wave source corresponds to the amplitude modulus of the acoustic waves at each point of a predetermined sphere centred on the source, divided by the maximum amplitude modulus along the sphere. In this way, the directivity pattern values are between zero and one.

A directivity pattern corresponds to the intersection of the radiation pattern with a plane. Therefore, it characterises the amplitude modulus variations on a circle of the plane centred on the source.

With reference to FIG. 5, the two opposite electrodes 406A, 406B are aligned along an axis A1 passing through the centre of the piezoelectric disk 402. These two electrodes 406A, 406B form a first dipolar source of acoustic waves (vibratory dipole) radiating a minimal acoustic field, for example zero, along an axis A2 passing through the centre of the piezoelectric disk 402 and different to the axis A1, the acoustic field being antisymmetric with respect to the axis A2 (same absolute value, but opposite signs, i.e. phase opposition).

In this way, with reference to FIG. 6, the first dipolar acoustic wave source has a first directivity pattern on the contact surface 104A or 104B, about the centre of the piezoelectric disk 402, with a minimal value, zero in the example described, along the axis A2 passing through the centre of the piezoelectric disk 402.

In the example described, the axis A2 is perpendicular to the axis A1. Preferably, the axes A1 and A2 are oriented with one perpendicular to the bottom edge of the object and the other parallel with the same edge.

In the example described, the directivity pattern of the source 406A, 406B is in the shape of an "8", and has a zero value in the direction of the axis A2. For example, the first directivity pattern, annotated $V1_{dir}$, is equal to $$V1_{dir} = \frac{\sqrt{\cos^2\alpha + \sin^2 2\alpha}}{\max_\alpha \sqrt{\cos^2\alpha + \sin^2 2\alpha}}$$

where $\alpha$ is the angle from the axis A1.

With reference to FIG. 7, as for the electrode 406A, 406B, the two opposite electrodes 408A, 408B are aligned along the axis A2 and form a second dipolar acoustic wave source (vibratory dipole) radiating a zero acoustic field along the axis A1 and antisymmetric with respect to the axis A1 (same absolute value, but opposite signs, i.e. in phase opposition).

In this way, with reference to FIG. 8, the second dipolar acoustic wave source has a second directivity pattern on the contact surface 104A or 104B, about the centre of the piezoelectric disk 402, having a minimal value, zero in the example described, along the axis A1.

In the example described, the directivity pattern of the source 408A, 408B is in the shape of "∞", with a zero value in the direction of the axis A1. For example, the second directivity pattern, annotated $V2_{dir}$, is equal to $$V2_{dir} = \frac{\sqrt{\sin^2\alpha + \sin^2 2\alpha}}{\max_\alpha \sqrt{\sin^2\alpha + \sin^2 2\alpha}}$$

where α is the angle from the axis A1.

In this way, each acoustic wave source is designed to emit, i.e. radiate, acoustic waves in the glass plate 102 according to the respective directivity pattern thereof, the two directivity patterns being concentric and different to each other.

By means of an inverse piezoelectric effect, the control signals generate acoustic waves in the glass plate 102, particularly antisymmetric Lamb waves characterised by the two displacement components thereof, in the plane of the plate and out of the plane (perpendicular to the plate plane). The disturbance created by touching the glass plate 102 essentially affects, by damping or blocking the contact surface, the out-of-plane displacement component (i.e. perpendicular to the glass plate 102).

In polar coordinates, the acoustic field out-of-plane component, annotated $S_1$, emitted by the first acoustic wave source 406A, 406B and observed at a distance r from the centre of the piezoelectric disk 402 and for an angle α, is similar to the control signal $e_1(t)$ of the acoustic wave source 406A, 406B further having a propagation interval $$\frac{2\pi}{\lambda}r,$$

where λ denotes the wavelength of the acoustic waves, and weighting corresponding to the directivity pattern. In the example described, the control signal $e_1(t)$ is sinusoidal $e_1(t)=E_{10} \sin(2\pi ft)$, such that the out-of-plane component $S_1$ is also sinusoidal and described by the components $$\begin{Bmatrix} S_{1x} \\ S_{1y} \end{Bmatrix}$$

thereof in Cartesian components with respect to the axes A1 and A2:

$$S_1(t, r, \alpha) = \begin{Bmatrix} S_{1x} \\ S_{1y} \end{Bmatrix} = \begin{Bmatrix} \cos(\alpha) \cdot A_{10} \cdot \sin\left(2\pi \cdot f \cdot t - \frac{2\pi}{\lambda}r\right) \\ \sin(2\alpha) \cdot A_{10} \sin\left(2\pi \cdot f \cdot t - \frac{2\pi}{\lambda}r\right) \end{Bmatrix},$$

where $A_{10}$ denotes the peak amplitude of the out-of-plane component $S_1$, proportional to the peak amplitude of the control signal $E_{10}$.

Similarly, in the example described, the control signal $e_2(t)$ is sinusoidal $e_2(t)=E_{20} \sin(2\pi ft)$, such that the acoustic field out-of-plane component $S_2$, due to the second acoustic wave source 408A, 408B, is also sinusoidal and described by the components $$\begin{Bmatrix} S_{2x} \\ S_{2y} \end{Bmatrix}$$

thereof in Cartesian coordinates with respect to the axes A1 and A2:

$$S_2(t, r, \alpha) = \begin{Bmatrix} S_{2x} \\ S_{2y} \end{Bmatrix} \begin{Bmatrix} \sin(2\alpha)A_{20} \cdot \sin\left(2\pi \cdot f \cdot t - \frac{2\pi}{\lambda}r\right) \\ \sin(\alpha)A_{20} \cdot \sin\left(2\pi \cdot f \cdot t - \frac{2\pi}{\lambda}r\right) \end{Bmatrix},$$

where $A_{20}$ denotes the peak amplitude of the out-of-plane component $S_2$, proportional to the peak amplitude of the control signal $E_{20}$.

The out-of-plane displacement components $S_1$ and $S_2$ (i.e. perpendicular to the glass plate 102) of the acoustic fields both correspond to bending modes and are thus sensitive to contact, for example to that of a finger on the glass plate 102.

The computer system device 424 is designed to weight the two control signals $e_1(t)$ and $e_2(t)$ and to vary this weighting over time. In the example described, the weighting is performed as follows: $k \cdot e_1(t)$ and $(1-k) \cdot e_2(t)$ where k varies between zero and one. This weighting variation gives rise to a corresponding variation of the amplitudes of the acoustic waves $S_1$ and $S_2$: $A_1 = k \cdot A_0$ and $A_2 = (1-k) \cdot A_0$, such that:

$$S_1(t, r, \alpha) = \begin{Bmatrix} S_{1x} \\ S_{1y} \end{Bmatrix} = \begin{Bmatrix} k \cdot \cos(\alpha) A_{10} \cdot \sin\left(2\pi \cdot f \cdot t - \frac{2\pi}{\lambda}r\right) \\ k \cdot \sin(2\alpha) A_{10} \cdot \sin\left(2\pi \cdot f \cdot t - \frac{2\pi}{\lambda}r\right) \end{Bmatrix}, \text{ and}$$

$$S_2(t, r, \alpha) = \begin{Bmatrix} S_{2x} \\ S_{2y} \end{Bmatrix} = \begin{Bmatrix} (1-k) \cdot \sin(2\alpha) A_{20} \cdot \sin\left(2\pi \cdot f \cdot t - \frac{2\pi}{\lambda}r\right) \\ (1-k) \cdot \sin(\alpha) A_{20} \cdot \sin\left(2\pi \cdot f \cdot t - \frac{2\pi}{\lambda}r\right) \end{Bmatrix}.$$

The two sources 406A, 406B and 408A, 408B are excited independently of each other, each generating a field characteristic of the geometry and orientation of the electrodes.

Inverse piezoelectric effect excitation of elastic waves is a linear and invariant process, such that the out-of-plane component of the total acoustic field generated by the first emitting device 304 is equal to the sum of the out-of-plane components of the two sources:

$$S(t, r, \alpha) = S_1(t, r, \alpha) + S_2(t, r, \alpha) = \begin{Bmatrix} S_{1x} + S_{2x} \\ S_{1y} + S_{2y} \end{Bmatrix},$$

i.e.:

$$S(t, r, \alpha) = \begin{Bmatrix} k \cdot \cos(\alpha) A_{10} \cdot \sin\left(2\pi \cdot f \cdot t - \frac{2\pi}{\lambda}r\right) + \\ (1-k) \cdot \sin(2\alpha) A_{20} \cdot \sin\left(2\pi \cdot f \cdot t - \frac{2\pi}{\lambda}r - \varphi\right) \\ k \cdot \sin(2\alpha) A_{10} \cdot \sin\left(2\pi \cdot f \cdot t - \frac{2\pi}{\lambda}r\right) + \\ (1-k) \cdot \sin(\alpha) A_{20} \cdot \sin\left(2\pi \cdot f \cdot t - \frac{2\pi}{\lambda}r - \varphi\right) \end{Bmatrix}$$

The first emitting device 304 thus generates acoustic waves wherein the spatial distribution of the amplitude at any frequency f varies as a function of k.

To illustrate this variation, if the two acoustic wave sources are controlled in phase with a zero phase shift φ and synchronously, i.e. at the same frequency, the total out-of-plane component S can be expressed according to a modulus and a phase, i.e. in complex annotation:

$$\overline{S}(t, r, \alpha) = \sqrt{\begin{aligned}&(k \cdot \cos(\alpha) \cdot A_{10} \cdot (1-k) \cdot \sin(2\alpha) \cdot A_{20})^2 + \\ &(k \cdot \sin(2\alpha) A_{10} \cdot (1-k) \cdot \sin(\alpha) \cdot A_{20})^2\end{aligned}} \cdot e^{j(2\pi \cdot f \cdot t - \frac{2\pi}{\lambda} r)}$$

In this way, the acoustic field out-of-plane component emitted, at the frequency f, by the first emitting device 304 is generally expressed as: $S(t,M,k)=A(M,k)\cdot\sin(2\pi\cdot f\cdot t-\phi(M))$, where M is a point on the touch surface 104A having the coordinates r, α. This out-of-plane component has an amplitude distribution A(M,k) at the frequency f, which varies as a function of k. This means that for two different values of k, the associated amplitude distributions are different and not mutually proportional.

In the case of the first emitting device, these amplitude distributions are all angular since A(M,k) is actually only dependent on the angle α.

To illustrate this variation in the amplitude distribution, various forms of the directivity pattern, according to the above equations and, if applicable, obtained experimentally, of the first emitting device 304 according to various values of k are illustrated in FIGS. 9 to 13. For the experimental results, a piezoelectric disk PZ26 measuring 30 mm in diameter and 0.5 mm in thickness attached to a borosilicate plate having the dimensions: 360 mm×220 mm×3.3 mm, was used. The speed vector was measured on a circle having an 80 mm radius centred on the piezoelectric disk. The signal frequency was f=40,400 Hz.

In the example described, the touch surface system 100 further comprises the second emitting device 306. As for the first emitting device 304, the out-of-plane component of the acoustic field S'(t,M,k) at the frequency f emitted by the second emitting device 306 is generally expressed as:

$$S'(t,M,k)=A'(M,k)\cdot\sin(2\pi\cdot f\cdot t\cdot\phi'(M)).$$

In this way, the total field out-of-plane component, at the frequency f, takes the same form: $S_{total}(t,M,k)=A_{total}(M,k)\cdot\sin(2\pi\cdot f\cdot \phi_{total}(M))$. According to the invention, the total acoustic field thus has an amplitude distribution $A_{total}(M,k)$ at the frequency f, which varies as a function of k. This means that for two different values of k, the associated amplitude distributions are different and not mutually proportional.

If the acoustic waves emitted are not monochromatic (i.e. at a single frequency), Fourier theory returns to the monochromatic case, by breaking down any signal into a sum of monochromatic signals.

With reference to FIG. 14, in the example described, the computer system device 424 is designed to increase k from zero to one in forty stages and to decrease the frequency f from one stage to the next, from 100 kHz to 20 kHz. It is advantageous to decrease the frequencies rather than the other way round, since high-frequency acoustic waves are propagated more quickly than lower-frequency acoustic waves. In this way, decreasing the frequencies prevents the first acoustic waves emitted being overtaken by subsequent waves.

In this way, the first control signal equals, for the stage i (i ranging from one to forty): $e_1(t)=k_i\cdot A_0 \sin(2\pi f_i t)$, whereas the second control signal equals, for the same stage i: $e_2(t)=(1-k_i)\cdot A_0 \sin(2\pi f_i t)$, where $k_1=0$, $k_{40}=1$ and $f_1=100$ kHz, $f_{40}=20$ kHz.

Preferably, each stage lasts a whole number of oscillation periods of the control signals $e_1(t)$ and $e_2(t)$.

In this way, at each stage, the first emitting device 304 emits an acoustic wave at the frequency $f_i$ and with an amplitude distribution:

$$A(M, k_i) = \sqrt{\begin{aligned}&(k\cdot\cos(\alpha)\cdot A_0\cdot(1-k)\cdot\sin(2\alpha)\cdot A_0)^2 + \\ &(k\cdot\sin(2\alpha)A_0\cdot(1-k)\cdot\sin(\alpha)\cdot A_0)^2\end{aligned}}.$$

In this way, the amplitude spectrum of each acoustic wave i is different to zero for the single frequency $f_i$. The amplitude spectrum of each acoustic wave thus has, at this frequency $f_i$, which is different in the example described from one emitted acoustic wave to another, an amplitude, varying in the medium according to a specific spatial distribution of the amplitude $A(M,k_i)$. Due to the variation of $k_i$ from one emitted acoustic wave to another, the spatial distributions of the amplitude $A(M,k_i)$ of the successive acoustic waves are mutually different.

Training and monitoring methods will now be described, using these spatial distribution variations.

With reference to FIG. 15, these methods use reference contacts C(i,j) wherein the positions on the contact surface 104B of the glass plate 102 are known by the computer system device 424. These reference contacts C(i,j) are for example distributed on a grid along the axes A1 and A2, where the indices (i,j) indicate the position thereof in the grid.

Furthermore, these methods use a proximity function V(C (i,j)), for determining the neighbouring reference contacts of a given reference contact (i,j). For example, if the reference contacts are distributed on a rectangular grid, the neighbouring reference contacts are the eight contacts surrounding the reference contact in question on the grid ("first ring") as illustrated in FIG. 15.

Moreover, in these methods, only the first emitting device 304 is taken into consideration, given that introducing the other emitting device 306 does not change, as explained above, the general expression of the total acoustic field in the plate.

With reference to FIG. 16, the training method 1600 first comprises a step 1602 during which the touch surface system 100 is placed in a quiet environment while the glass plate 102 is left without contact.

Under these conditions, during a step 1604, the computer system device 424 supplies the control signals $e_1(t)$ and $e_2(t)$ as represented in FIG. 14, to the first emitting device 304, and the latter emits acoustic waves in the glass plate 102.

At the same time, during a step 1606, the receiving device 308 receives the acoustic waves after the propagation thereof in the glass plate 102, and supplies the computer system device 424 with an off-load reception signal, annotated r(t), corresponding to the acoustic waves received. The off-load reception signal r(t) lasts for all the successive spatial distributions.

During a step 1608, the computer system device 424 calculates the amplitude of the Fourier transform of the off-load reception signal r(t), referred to as the off-load spectral amplitude R(f)=|fft(r(t))|.

During a step 1610, a reference contact C(i,j) is applied on the contact surface 104A of the glass plate 102, again in a quiet environment.

During a step 1612, with the reference contact C(i,j) applied, the computer system device 424 supplies the control signals $e_1(t)$ and $e_2(t)$ to the first emitting device 304.

During a step 1614, the first emitting device 304 emits acoustic waves corresponding to the control signals $e_1(t)$ and $e_2(t)$ in the glass plate 102, while the receiving device 308, during a step 1616, receives the acoustic waves after the propagation thereof in the glass plate 102, and supplies the computer system device 424 with the corresponding reception signal, referred to as the reference reception signal $r_{i,j}(t)$.

During a step 1618, the computer system device calculates the amplitude of the Fourier transform of the reference reception signal $r_{i,j}(t)$, referred to as the reference spectral amplitude $r_{i,j}(f)=|fft(r_{i,j}(t))|$.

During a step 1620, the computer system device 424 calculates a distance, referred to as the reference spectral amplitude distance DNR(i,j), between the off-load amplitude and the reference amplitude. For example, the reference spectral amplitude distance DNR(i,j) is a relative standardised distance, for example equal to the standard 1 of the percentage of variation of the off-load $R(f)=|fft(r(t))|$ and reference spectral amplitudes $R_{i,j}(f)=|fft(r_{i,j}(t))|$:

$$DNR(i,j) = \sum_f \left| \frac{R_{i,j}(f) - R(f)}{R(f)} \right| = \sum_f \left| \frac{R_{i,j}(f)}{R(f)} - 1 \right|.$$

The method 1600 then returns to the step 1610, for a further reference contact C(i,j), until all the reference contacts have been scanned.

It may be observed that it is only necessary to carry out the training method 1600 on one of the two contact surfaces 104A, 104B, since two facing contacts on either side of the glass plate 102 have the same effect on the acoustic waves propagated in the glass plate 102.

Moreover, the Fourier transform of the reception signal is preferably performed on approximately 16,000 points (or at least 4096 points or 1024 points).

With reference to FIG. 17, a monitoring method 1700 using the touch surface system 100 first comprises initialisation steps 1702 to 1712.

During a step 1702, the touch surface system 100 is placed, without any contact being applied thereon, in the operating environment thereof, potentially comprising a residual noise vibrating the glass plate 102 and thus producing an interfering signal in the reception signal supplied by receiving device 306. The residual noise may also come from the processing electronics, particularly quantification noise.

During a step 1704, the computer system device 424 supplies the control signals $e_1(t)$ and $e_2(t)$ to the first emitting device 304, and the emitting device 304 emits the corresponding acoustic waves in the glass plate 102.

At the same time, during a step 1706, the receiving device 308 receives the acoustic waves after the propagation thereof in the glass plate 102, and supplies the computer system device 424 with a reception signal, referred to as the reception signal with residual noise $r_{BR}(t)$, corresponding to the acoustic waves received.

During a step 1708, the computer system device 424 calculates the amplitude of the Fourier transform of the reception signal with residual noise $r_{BR}(t)$, referred to as the spectral amplitude with residual noise $R_{BR}(f)=|fft(r_{BR}(t))|$.

During a step 1710, the computer system device 424 calculates an initial residual noise BRD on the basis of the spectral amplitude with residual noise $R_{BR}(f)$ and the off-load spectral amplitude R(f). For example, the initial residual noise BRD is the standard 1 of the percentage of variation of the spectral amplitudes with residual noise $R_{BR}(f)$ and off-load R(f):

$$BRD = \sum_f \left| \frac{R_{BR}(f)}{R(f)} - 1 \right|.$$

During a step 1712, the computer system device 424 sets, to the initial residual noise value, a data item BR representing the current residual noise, i.e. the operation: BR←BRD. Moreover, the computer system device 424 sets an iteration counter n to the value 1, i.e. the operation: n←1.

The monitoring method 1700 thus comprises the loop of monitoring steps 1714 to 1750, the current iteration of the loop of steps being the iteration n. During a step 1714, the computer system device 424 supplies the control signals $e_1(t)$ and $e_2(t)$ to the first emitting device 304, and the emitting device 304 emits the corresponding acoustic waves in the glass plate 102.

At the same time, during a step 1716, the receiving device 308 receives the successive acoustic waves after the propagation thereof in the glass plate 102, and supplies the computer system device 424 with a reception signal, referred to as the current reception signal $r_n(t)$, corresponding to the acoustic waves received.

During a step 1718, the computer system device 424 calculates the amplitude of the Fourier transform of the current reception signal $r_n(t)$, referred to as the current spectral amplitude $R_n(f)=|fft(r_n(t))|$.

During a step 1720, the computer system device 424 calculates a current spectral amplitude distance DNR, on the basis of the spectral amplitude with residual noise $R_{BR}(f)$ and current spectral amplitude $R_n(f)$. For example, the current spectral amplitude distance $DNR_n$ is a relative standardised distance, for example the standard 1 of the percentage of variation of the spectral amplitude with residual noise $R_{BR}(f)$ and current spectral amplitude $R_n(f)$:

$$DNR_n = \sum_f \left| \frac{R_n(f)}{R_{BR}(f)} - 1 \right|.$$

During a step 1722, the computer system device 424 calculates a current disturbance $PC_n$ on the basis of the current spectral amplitude distance $DNR_n$ and the residual noise BR. For example, the current disturbance $PC_n$ is the percentage of variation between the current spectral amplitude distance $DNR_n$ and the residual noise BR:

$$PC_n = \left| \frac{DNR_n}{BR} - 1 \right| \times 100.$$

During a step 1724, the computer system device 424 determines whether the current disturbance $PC_n$ has deviated slightly with respect to the previous iteration, indicating a variation in the residual noise, but not contact since the latter would give rise to great variation in the current disturbance $PC_n$. This slight deviation is for example determined if:

$$\left|\frac{PC_n}{PC_{n-1}} - 1\right| \times 100 \leq 15\%.$$

If a slight deviation of the current disturbance $PC_n$, is determined, the steps 1726 to 1730 are executed.

During the step 1726, the computer system device 424 updates the spectral amplitude with residual noise $R_{BR}$ (f) to the value of the current spectral amplitude $R_n$(f), i.e. the operation: $R_{BR}(f) \leftarrow R_n(f)$.

During the step 1728, the computer system device 424 calculates the new residual noise BR on the basis of the updated spectral amplitude with residual noise $R_{BR}$(f), i.e.:

$$BR = \sum_f \left|\frac{R_{BR}(f)}{R(f)} - 1\right|.$$

During the step 1730, the computer system device 424 increments n by one unit and the method returns to the steps 1714 and 1716.

If no slight deviation of the current disturbance $PC_n$ is determined, during a step 1732, the computer system device 424 determines whether the current disturbance $PC_n$ is high, for example greater than a predetermined threshold, which would indicate the occurrence of contact. For example, contact C is detected if: $PC_n \geq 100\%$.

If contact C is detected, during a step 1734, the computer system device 424 calculates the deviations between the reference spectral amplitude distance DNR(i,j) and the current spectral amplitude distance $DNR_n$. In the example described, these deviations are relative standardised deviations, for example expressed as percentages of the residual noise. Also in the example described, these deviations are placed in a matrix $ENRD_n(i,j)$ where each element j) of the matrix corresponds to the deviation with respect to the reference contact C(i,j):

$$ENRD_n(i, j) = \left|\frac{DNR_n - DNR(i, j)}{BR} - 1\right| \times 100.$$

During a step 1736, the computer system device 424 determines the closest reference contact C(i,j) to the detected contact C. It consists of the reference contact associated with the smallest element of the matrix $ENRD_n(i,j)$ (i.e. the element indicating the smallest deviation with respect to the current spectral amplitude distance $DNR_n$). This smallest element is annotated $ES_n = ENRD(i_n, j_n)$, where $(i_n, j_n)$ is the position thereof in the matrix $ENRD_n(i,j)$ and also in the reference contact grid.

In one simple alternative embodiment of the invention, the computer system device 424 supplies, the position of the detected position C, the position of the closest reference contact $C(i_n, j_n)$, and the method 1700 goes to the step 1750.

However, in the example described, the position of the detected contact C is refined.

In this way, during a step 1738, the computer system device 424 determines whether the detected contact C is close to the closest reference contact $C(i_n, j_n)$ or not, by means of a proximity condition.

For this purpose, in the example described, this determination is carried out by calculating a contrast ratio $RC_n$ between the smallest element $ES_n$ and the other elements of the matrix $ENRD_n(i,j)$. For example, the contrast ratio $RC_n$ is calculated with:

$$RC_n = \frac{\langle ENRD_n(i, j)\rangle_{i,j}}{ES_n} \times 100.$$

Then, the computer system device 424 determines whether the detected contact C is close to the closest reference contact $C(i_n, j_n)$ or not on the basis of the contrast ratio $RC_n$. In the example described, the detected contact C is closest to the closest reference contact $C(i_n, j_n)$ if the contrast ratio is greater than a predetermined value, for example if: $RC_n \geq 150$.

During a step 1740, if the detected contact is determined as being close to the closest reference contact $C(i_n, j_n)$, then the computer system device 424 supplies, as the position of the detected contact C, the position of the closest reference contact $C(i_n, j_n)$. The method 1700 then goes to the step 1750.

During a step 1742, if the detected contact is not determined as being close, according to the proximity condition, to the closest reference contact $C(i_n, j_n)$, then the computer system device 424 determines the position of the contact C on the basis of the positions of the closest reference contact $C(i_n, j_n)$ and the neighbouring reference contacts thereof, according to the predetermined proximity function $V(C(i_n, j_n))$.

More specifically, during a step 1744, the computer system device 424 calculates an equivalent mass $M_n(i,j)$ for each element of the matrix $ENRD_n(i,j)$, the equivalent mass $M_n(i,j)$ increasing as this element, corresponding to a deviation with the respect to the current spectral amplitude distance $DNR_n$, decreases (inverse function or equivalent). In the example described, the equivalent mass $M_n(i,j)$ is calculated with:

$$M_n(i, j) = \frac{ES_n}{ENRD_n(i, j)}.$$

During a step 1746, the computer system device 424 calculates the barycentre of the reference contacts C(i,j), weighted by the corresponding equivalent mass thereof, situated in the vicinity $V(C(i_n, j_n))$ about the closest reference contact $C(i_n, j_n)$.

During a step 1748, the computer system device 424 supplies, as the position of the detected contact C, the barycentre calculated in this way.

Whether a contact is detected in the step 1732 or not, during the step 1750, the computer system device 424 increments n by one unit and the method returns to the steps 1714 and 1716.

It should be noted that, during monitoring, the control signals are generated with a period of 100 Hz and the Fourier transforms are performed continuously on an acquisition window of approximately 16,000 points at a sampling frequency of 1.6 Msamples/s (i.e. 100 Hz) with 12-bit signal quantification.

Moreover, it should be noted that, if the touch surface system 100 is designed to detect and locate the touch of a finger, the spacing of the reference contact grid is preferably less than or equal to the characteristic size of the finger. To give an order or magnitude, the contact surface area of a forefinger is approximately 1.3 $cm^2$ and the characteristic touch size is approximately 12 mm. In this way, the spacing of the grid is preferably less than 1 cm, for example equal to 6 mm. Moreover, the training reference contacts have a similar characteristic size to that of a finger. In this way, by means of the previous grid spacing, these reference contacts overlap with each other. This makes it possible to obtain a lower number of reference contacts while offering a high resolution, less than one millimeter, by means of the barycentre calculation. Moreover, this makes it possible to reduce position recognition errors when the touch is dragged slowly and continuously from one reference contact to another. Having partial overlapping of the reference contacts thus ensures that a touch is located more precisely. The reliability is also increased in that touch is not detected with respect to a single reference contact, but with respect to a plurality of reference contacts situated in the same proximity. The overlap of two adjacent reference contacts should thus be sufficient so that the disturbances are relatively similar and the barycentre calculation makes sense. In other words, the spacing of the grid should be sufficiently fine in relation to the characteristic size of the finger so that random positioning of the finger on the touch area always overlaps sufficiently with a reference contact. This ensures that the contrast level threshold is always reached following touching, particularly when touching occurs in the centre of two reference contacts. However, the grid spacing should remain as large as possible so as not to increase the number of reference contacts, and thus the training time, unnecessarily.

Moreover, if the grid spacing is much smaller than the characteristic touch radius, the proximity area may be extended to a second or a third ring of reference contacts. The number of rings is for example equal to the characteristic radius divided by the grid spacing. For a grid spacing of 3 mm, two reference contact rings will be adopted for example.

In one enhancement, the position refined by means of the barycentre calculation may then be realigned on a grid having a higher resolution. The position and movement of the finger are thus measured relatively precisely on this higher resolution grid. For example, the reference contact grid may have a 6 mm spacing, whereas the high resolution grid may be that of a graphic display screen typically having a 0.3 mm spacing. In this way, in the case of an HD screen comprising 1920×1080 pixels with a 0.3 mm spacing, i.e. 576×324 mm (66 cm or 26 inches diagonally), the reference contact grid is reduced, with respect to the high resolution grid, to 97×55 i.e. 5335 points, i.e. a reduction by almost a factor of 400 while retaining a fine adjustment of the touch on the high resolution grid.

Moreover, the method for refining the location of the detected contact may be enhanced further. Indeed, the method in FIG. 17 involves the drawback that the barycentre as calculated tends to be situated near the closest reference contact, even if the detected contact is considerably "offset" from the closest reference contact, i.e. almost midway between an adjacent reference contact.

To remedy this problem, the method 17 may be enhanced to overweight the reference contacts adjacent to the closest reference contact. This makes it possible to offset the location of the detected contact with respect to the closest reference contact and thus correctly locate the contacts occurring midway between two reference contacts. To amplify the effect, it is also possible to define the equivalent masses on the basis of the square, cube or a higher power of the deviations $ENRD_n(i,j)$.

Another way of enhancing the location to midway between two adjacent reference contacts consists of determining the position of the (detected) contact on the basis of a sigmoid or hyperbolic tangent non-linear function of the barycentre with respect to the position of the closest reference contact. Such a function makes it possible to amplify the small distances from the barycentres with respect to the closest reference contact, while limiting the position of the mid-way contact. In this way, it is possible to take:

$$\begin{cases} X_{HD} = X_{zi} + \frac{1}{2}\text{Tanh}(a(X_g - X_{Zi})) \\ Y_{HD} = Y_{zi} + \frac{1}{2}\text{Tanh}(a(Y_g - Y_{Zi})) \end{cases},$$

where $X_{HD}, Y_{HD}$ are the coordinates of the detected contact, $X_{zi}, Y_{zi}$ the coordinates of the closest reference contact, $X_g, Y_g$ the coordinates of the barycentre and $\alpha$ the displacement amplification factor which may typically be equal to between 5 and 10.

With reference to FIG. 18, a second touch surface system 1800 according to the invention comprises a rectangular glass plate 1802 having a periphery 1804.

The touch surface system 1800 further comprises a device for emitting acoustic waves 1806 arranged in a corner 1804 of the periphery where two edges 1808, 1810 of the plate 1802 join.

The emitting device 1806 comprises two acoustic wave sources 1812, 1814. The sources 1812, 1814 are elongated and extend along the edges 1808, 1810, respectively.

In the example described, the emitting device 1806 comprises a piezoelectric square 1816 provided with two arms 1818, 1820, for example rectangular, perpendicular to each other and extending along the two edges 1808, 1810, respectively. The square 1816 has a bottom face covered with a lower electrode 1817 and a top face covered with three upper electrodes: two electrodes 1822, 1824 extending on the two arms, respectively, and one electrode 1826 extending to the centre of the square, at the join of the two arms. The latter electrode is connected to the lower electrode to form an earth return. The acoustic wave sources comprise the arms 1818, 1820 provided with the electrodes thereof, respectively.

The touch surface system 1800 further comprises a device for receiving acoustic waves 1828. The receiving device 1828 may be arranged anywhere on the plate 1802, but preferably at a distance from the emitting device 1806. In the example described, the receiving device 1828 is situated in another corner 1830 of the plate 1802. This makes it possible to reduce the acoustic waves received directly by the receiving device 1828 to prioritise those diffracted by contact on the plate 1802.

The receiving device 1828 comprises a piezoelectric arm 1832, for example rectangular, having a bottom face covered with a lower electrode 1834 and a top face covered with an upper electrode 1836.

The touch surface system 1800 further comprises a computer system device 424 similar to that in the example in FIGS. 1 to 17.

The lower electrodes are thus all connected to the ground, and consequently also the central electrode 1826. The control signals $e_1(t)$ and $e_2(t)$ are applied between the central ground electrode 1826 and the electrodes 1822, 1824 of the arms of the emitting device 1806. The control signals thus have a single "phase", i.e. a single potential different from ground. Moreover, the reception signal $r(t)$ is collected between the lower electrode 1834 and the upper electrode 1836 of the receiving device 1828.

Alternatively, the upper electrodes 1822, 1824 are each split into two separate sub-electrodes of equal surface areas, to which the control signal $e_1(t)$ or $e_2(t)$ is applied. Each control signal thus has two "phases", i.e. two potentials different from ground applied to the two sub-electrodes, respectively.

This form of touch surface system is very suitable for small graphic displays, for example measuring seven to ten inches diagonally.

Moreover, preferably, the emitting device 1806 is controlled so as to emit acoustic waves having a frequency between one and one hundred kilohertz.

Preferably, the arms 1818, 1820 of the piezoelectric square 1816 have a length several times the wavelength associated with the central frequency of the excitation spectrum of the acoustic waves emitted, for example two to five times.

With reference to FIG. 19, a contactless interface system 1900 according to one possible embodiment of the invention comprises a flat or slightly curved plate 1902, for example made of glass, surrounded by air 1903.

The interface system 1900 further comprises a device 1904 for emitting acoustic waves 1906 in air along the plate 1902.

More specifically, the emitting device 1904 comprises a resonating disk 1908, for example made of metal, having a periphery 1910 and a central part 1912 tapering from the periphery to the centre of the disk 1908, to a central opening. The resonating disk 1908 further comprises a hollow central sleeve 1914 extending perpendicular to the disk 1908 from the periphery of the central opening, via an opening provided in the plate 1902. The periphery 1910 of the resonating disk 1902 has a bottom face (facing the plate 1902) covered with a piezoelectric ring 1915, covered with electrodes similar to the piezoelectric disk 402 in FIG. 4. In this way, the piezoelectric ring has a bottom face covered with a lower electrode and a top face wherein the respective quarters are covered with four upper electrodes, two whereof can be seen in FIG. 19.

The sleeve 1914 passes through the plate 1902 without touching same and emerges to rise from the plate 1902 by a height preferentially in the region of the half wavelength of the acoustic waves propagated in air, i.e. 7.5 mm at 23 kHz above the surface (or 3.5 mm at 45 kHz). The sleeve 1914 is closed on the side emerging through the plate 1902.

The interface system 1900 further comprises a device 1916 for receiving the acoustic waves 1906 propagated in air 1903 along the plate 1902. For enhanced reception of the waves emitted in air, the receiving device 1916 comprises a resonating disk 1918 similar to the disk 1908, with a piezoelectric ring 1919 covered with a lower electrode and four upper electrodes of the same size as that of the disk 1908, conferring at least the same resonance frequencies, except that it can detect more resonance frequencies using only one of the signals obtained between one of the four upper electrodes and the ground. The reception signal may also supply a differential signal from two quarters of opposite electrodes by the top or two half-rings (by joining two adjacent quarters of electrodes) such that the reception range thereof always contains at least the same frequencies as that of the emitting transducer 1908.

This two-source electric design using four paired electrodes makes it possible, for the emitting device, to generate bending movements of the emitting sleeve radiating in the ambient air of the acoustic waves parallel with the plane of the plate and, for the receiving device, detecting these air waves in the same frequency band corresponding to maximum sensitivity.

The interface system 1900 further comprises a computer system device (not shown) similar to that in FIGS. 1 to 17, and connected to the electrodes of the emitting 1904 and receiving devices 1916 in the same way, such that the emitting device receives the control signals $e_1(t)$ and $e_2(t)$, and that the receiving device supplies the reception signal $r(t)$.

An example of design of the piezoelectric disks 1908 and 1918 is illustrated in FIG. 20.

With reference to FIG. 21, the electrodes of the emitting device 1904 include four electrodes 2102A, 2102B, 2104A, 2104B respectively covering the four quarters of the top face of the piezoelectric ring 1915. The pairs of two opposite electrodes 2102A, 2102B and 2104A, 2104B are intended to be connected to receive the control signals $e_1(t)$ and $e_2(t)$ as in the example in FIGS. 1 to 17. In FIG. 21, the feasibility of vibrating the sleeve 1914 using a control signal was tested by subjecting one of the two pairs of electrodes to a periodic signal having a variable frequency and amplitude 20 Vcc.

With reference to FIG. 22 representing the amplitude of variation of the sleeve 1914 as a function of the control signal, the resonating disk 1908 has a resonance frequency at 22950 Hz at which the amplitude of vibration of the sleeve 1914, measured with a laser vibrometer, is six microns peak-to-peak.

In this way, it is possible to obtain vibration of the sleeve by a few microns, sufficient to generate airborne acoustic waves along the plate 1902, using a control signal of a few Volts.

The interface system 1900 operates as follows.

The computer system device supplies the control signals $e_1(t)$ and $e_2(t)$ to the emitting device 1904.

In response, the resonating disk 1908 of the emitting device 1904 starts vibrating.

The central part 1912 amplifies the mechanical vibration such that the sleeve 1914 tilts and vibrates, according to the amplitude weightings of the control signals $e_1(t)$ and $e_2(t)$.

The sleeve 1914 forms an impedance adaptation area effectively transmitting the mechanical waves as airborne acoustic waves 1906 flush with the plate 1802, according to a weighting-dependent directivity pattern.

In this way, according to the successive weightings, the airborne acoustic waves 1906 successively exhibit spatial distributions of the amplitude in air 1903 at the surface of the plate 1902, which are mutually different.

In a similar manner to that described for the system in FIGS. 1 to 17, the computer system device detects and locates the presence of disturbance in the air at the surface of the plate 1902 created by an obstacle such as a finger, on the basis of the reception signal $r(t)$. The disturbance starts to be detectable from a specific approach distance from the obstacle, which is adjustable from a few millimeters to a few centimeters from the plate 1902 according to the height of the part of the sleeve emerging above the glass plate 1902.

With reference to FIG. 23, an interface system 2300 with and without contact according to the invention is practically identical to the interface system 1900 in FIG. 19, so that the same references are used for identical elements.

The emitting device 1904 of the interface system 2300 further comprises a peripheral rib 2302 extending on the inner face of the periphery of the piezoelectric disk, and attached to the plate 1902 such that some of the mechanical vibrations are transmitted as seismic acoustic waves 2304 in the plate 1902, in the same way as in the system in FIGS. 1 to 17, whereas another portion of the mechanical vibrations are transmitted in the air close to the plate 1902 as airborne acoustic waves 1906.

The receiving device 1916 is modified in the same way as the emitting device 1904.

Preferably, the emitting device 1904 is designed such that the proportion of waves emitted in the two media is comparable. Since solid-solid coupling between the emitting device and the plate 1902 is more effective than solid-air transmission, contact via the rib 2302 is sufficient. Obviously, any other type of contact could also be suitable.

The disturbance thus starts before contact occurs due to the disturbances of the air waves.

The training method is thus modified to include two training processes: one corresponding to contactless disturbance, i.e. only of the air waves, the other corresponding to disturbance with contact, i.e. simultaneous disturbance of airborne acoustic waves and seismic acoustic waves. The excitation range for the seismic part may be broadband and distributed for example over forty frequencies between 20 kHz and 100 kHz as in the previous case, whereas the excitation and reception of the air waves will be carried out at only one (for example 22,950 Hz) or two resonance frequencies (for example 22,950 Hz and 65,850 Hz) involving bending of the sleeve.

This design makes it possible to attach the emitting and receiving transducers to the wall of the plate by bonding. The direct coupling between the two transducers via the plate and via the air is thus stable and independent of any other supporting device. The transducers remain mechanically coupled with the outside world via small diameter coaxial cables, typically less than one millimeter representing a constant slight disturbance. Moreover, in the case of the assembly in FIG. 23, the holes produced to insert the sleeve are tight so that the plate can form one of the walls of a closed and/or tight cage. The ambient air may optionally be replaced by any other gas, or any other fluid, in particular a liquid and the cage may form a receptacle such that localised interaction may consist either of finger contact on the outer face of the receptacle or the presence of a disturbance in the liquid consisting of an interruption in mechanical impedance (passage of a small fish in the vicinity of the wall, appearance of an air bubble, etc.).

Alternatively, the resonating disk is arranged on the side of the plate when the disturbance is to be detected and the sleeve extends opposite the contact between the disk and the plate. In this way, the sleeve does not pass through the plate and it is not necessary to drill same.

Alternatively, the sleeve extends on either side of the central area, tapering and enabling impedance adaptation. The sleeve is then open on one side and closed on the other, or is open on both sides. In this alternative embodiment, it is possible to detect disturbances, with and without contact, on each face of the plate.

In an enhancement, in order to facilitate air wave detection in the vicinity of the plate surface, a tube arc forming an "ear antenna" may be attached to the surface of the plate, for example in a corner thereof. The tube arc is preferably concentric with the sleeve of the receiver and of the same height. The thickness of the tube arc may for example be some tens of millimeters to some millimeters.

The tube arc increases the collecting surface area receiving the waves diffracted by the presence of the finger or an object in the monitoring area and reflects same to the sleeve. For example, the tube arc covers an angular sector equal to 90° in the direction of the space wherein the airborne interactions occur.

The tube arc is for example machined in the same material as that used for machining the resonating disk. In this case, the tube arc extends preferably in a circular manner, with an inner tube arc radius equal to that of the resonating disk.

Alternatively, the tube arc is made of a separate part for example moulded in a plastic which is then attached to the plate on the side where the sleeve is situated (or both sides of the plate in the case of two sleeves), at a greater distance from the resonating disk. In this case, the tube arc has a parabolic profile, the focal point thereof merging with the central axis of the sleeve. This profile is suitable for detecting disturbances at a distance from the receiving device.

The tube arc also enables the receiving device to detect airborne acoustic waves received in the audible range and thus function as a microphone. The receiving device thus functions as a dual-medium sensor for locating a disturbance with and without contact and for detecting sounds in a specific frequency band, for example in the audible frequency band for voice interaction.

Moreover, again in an enhancement, a tube arc may also be arranged about the emitting device, so as to increase the intensity of the acoustic field emitted by the emitting device along the face of the plate to be monitored.

In the case of acoustic wave emission in a fluid, particularly in water or air, the waves are compression waves and the acoustic energy, even restricted to the ultrasonic band, may impair auditory perception at high outputs and in the case of prolonged exposure. Excitation should thus be performed while providing people and living beings with hearing protection and by amplifying the signal received typically by a gain of 40 to 80 dB and by limiting the excitation amplitude to a level compatible with safety thresholds. For a clearer idea, a vibration having an amplitude of 1 µm in air at 23 kHz generates a dynamic pressure of 64 Pa, i.e. approximately 130 dB acoustic equivalent (if our hearing threshold of $2 \cdot 10^{-5}$ Pa were to remain valid at 23 kHz). The ultrasonic mechanical energy, even not perceived by the receptors in the ear, should be limited. This is possible optionally by performing, in addition to the amplification of the signal received in conjunction with the limitation of the excitation signal, an intermittent excitation, generating in the medium a lower mean exposure value, typically less than 85 dB at a distance of 1 cm from the source, for a pressure reference of $2 \cdot 10^{-5}$ Pa. In this way, the acoustic energy emitted in the fluid may, occasionally over time, be greater than 85 dB, particularly very near the source, but remains on average over time and throughout the fluid medium less than 85 dB for the ultrasonic range and obviously also for the audible range.

Moreover, in the event of amplification, detection of slight disturbances is facilitated if the gain is chosen so that the maximum peak-to-peak amplitude of the off-load signal received (i.e. contactless) reaches the full scale of the Analogue to Digital Converter (ADC) used and if the signal-to-noise ratio is enhanced by performing, following the amplification, band-pass filtering corresponding to the excitation spectrum used (example 20 kHz-100 kHz).

In a further embodiment of the invention, a similar system to those described above could be used in the field of non-destructive testing. Indeed, any other cause of interruption of impedance on the surface of or inside an object will cause a disturbance suitable for being detected using seismic acoustic waves emitted with spatial distributions of the amplitude in the object at respective frequencies, which are mutually different, as explained above. These causes may be minor wear defects or fatigue defects in the materials, particularly cracks or chips in elongated materials having a constant cross-section such as rails, tubes, rods, wherein the cross-section should remain intact over lengths greater than the area of coverage of the transducers, but also localised delamination appearing on surface materials such as blades, shells, plates.

Since the location method described above is extremely sensitive to very slight disturbances, it will be advantageously used for detecting very small cracks or very small areas of delamination, or for detecting the presences of drops on a windshield surface, quantities of bubbles or density fluctuations in a liquid contained in a container, or monitoring or characterising the aging of a food product. For all these scenarios, an acoustic pulse in the form of a glitch with frequency modulation having spatial distribution of the amplitude varying over time, such as the emitting devices described above and wherein the radiation pattern varies over time, is emitted in the medium where a disturbance is liable to occur. These acoustic waves are first emitted during a training phase with typical disturbances to obtain reference reception signals, and then during a monitoring phase where the reception signal is compared to the reference reception signals.

Moreover, the methods for detecting and locating a disturbance, particularly a contact, described above could be modified to detect multiple disturbances.

Indeed, in that the reception signal is standardised in relation to the reference reception signals corresponding to single disturbances, it is possible to detect multiple disturbances by increasing the training set of the linear combinations of single disturbances.

This property was checked experimentally on a touch surface system such as that in FIGS. 1 to 17, but with a Nylon polyamide PA12 plastic shell as the supporting member rather than a glass plate. The reason is as follows: if the radiation pattern has slow spatial variation, i.e., in the Fourier space, associated with lower spatial frequencies than those of the finger or the disturbance, which is the case for dipolar radiations, the disturbance is proportional to the contact surface area. This is all the more applicable if the disturbance of the bulk waves is low overall and the disturbance due to viscous damping, a non-linear phenomenon dependent on the vibration rate, is lower. This leaves only the disturbance associated with the wave diffraction phenomenon, the field received diffracted by the multiple interaction(s) being, according to the Huygens-Fresnel principle, the Kirchhoff-Sommerfeld integral applied to the interaction surface(s). However, according to the Huygens-Fresnel principle, each interaction area acts as a secondary source point distribution. The total diffracted field for a multiple contact is thus indeed the sum of the diffracted fields for isolated contacts. This reasoning particularly applies in air where there is practically no viscous damping, but only air wave diffraction.

With reference to FIG. 24, the first curve shows the frequency amplitude of the standardised reception signal in relation to a contact at a position A of the shell. The second curve shows the frequency amplitude of the standardised reception signal in relation to a contact at a position B of the shell. In addition, the lower curve shows the overlap of the sum of the first two curves and the curve obtained by means of direct training by simultaneously applying two contacts at the positions A and B. Accounting for the contact positioning errors, it is observed that the two curves are almost identical and thus the total disturbance is the sum of the individual disturbances.

It is obvious that systems such as those described above are suitable for detecting and locating a disturbance without requiring acoustic wave guides, or making transit time calculations.

With reference to FIGS. 25 and 26, control signals other than those described above could be used.

For example, one advantageous particular scenario would be that of taking the out-of-plane component of the total acoustic field described above:

$$S(t, r, \alpha) = \begin{cases} k \cdot \cos(\alpha) A_{10} \cdot \sin\left(2\pi \cdot f \cdot t - \frac{2\pi}{\lambda}r\right) + \\ (1-k) \cdot \sin(2\alpha) A_{20} \cdot \sin\left(2\pi \cdot f \cdot t - \frac{2\pi}{\lambda}r - \varphi\right) \\ k \cdot \sin(2\alpha) A_{10} \cdot \sin\left(2\pi \cdot f \cdot t - \frac{2\pi}{\lambda}r\right) + \\ (1-k) \cdot \sin(\alpha) A_{20} \cdot \sin\left(2\pi \cdot f \cdot t - \frac{2\pi}{\lambda}r - \varphi\right) \end{cases}$$

setting $k=0.5$, and introducing a phase shift $\varphi$ between the two dipolar sources:

$$S(t, r, \alpha) = \begin{cases} 1/2 \cdot \cos(\alpha) A_{10} \cdot \sin\left(2\pi \cdot f \cdot t - \frac{2\pi}{\lambda}r\right) + \\ 1/2 \cdot \sin(2\alpha) A_{20} \cdot \sin\left(2\pi \cdot f \cdot t - \frac{2\pi}{\lambda}r - \varphi\right) \\ 1/2 \cdot \sin(2\alpha) A_{10} \cdot \sin\left(2\pi \cdot f \cdot t - \frac{2\pi}{\lambda}r\right) + \\ 1/2 \cdot \sin(\alpha) A_{20} \cdot \sin\left(2\pi \cdot f \cdot t - \frac{2\pi}{\lambda}r - \varphi\right) \end{cases}$$

The amplitudes of the control signals $e_1(t)$ and $e_2(t)$ are thus constant over time and the frequencies thereof are the same. The parameter which changes is the phase shift $\varphi$ between the control signals and thus between the two dipolar sources.

FIGS. 25 and 26 illustrate the directivity patterns observed experimentally on a plate having the dimensions 360 mm×220 mm×3.3 mm for $\varphi=0$ and $\varphi=\pi/2$. The other parameters are $f=40,400$ Hz, $k=0.5$, $E_{01}=E_{02}=20$ Volts, such that $A_{01}=A_{02}$. It is thus possible to radically change the directivity pattern merely by changing the phase shift between the control signals $e_1(t)$ and $e_2(t)$ for example in 40 stages at 2° intervals between 0 and 90°.

With reference to FIG. 27, an interface system 2700 with and without contact, designed to further produce vibrotactile feedback in the glass plate will now be described.

The system 2700 comprises the same elements as the system in FIG. 19, with furthermore a movable vibration part 2702 inserted in the sleeve of the resonating disk 1910. The movable part comprises a rod 2704 inserted in the sleeve and extending along the axis thereof. The movable part further comprises a weight 2706 attached to the rod offset in relation to the rod axis. The weight is for example in the shape of a half-disk and is preferably situated on the other side of the resonating disk as the sleeve.

The movable part is trapped in the sleeve, but may continue to rotate about the rod axis.

A vibrotactile feedback may thus be generated, for example, to confirm an action or a selection by a user operating the interface system, by supplying mutually squared sinusoidal control signals $e_1(t)$ and $e_2(t)$, at the resonance frequency of the resonating disk, for example at 22,950 Hz. By means of such control signals, the weight is rotated with a speed directly dependent on the amplitude of the ultrasonic vibration of the sleeve.

For example, it was found that, for an inner sleeve diameter of 3 millimeters, the movable part may rotate at a speed that can readily reach 100 to 200 revolutions per second, thus producing a strong vibration transmitted in the shell or the plate. To prevent the rotation of the weight, it is simply necessary to supply control signals in phase with each other and with a lower intensity.

Alternatively, the movable vibration part may advantageously be housed in the sleeve of the receiving device, but switched to emitting mode when the application of vibrotactile feedback is sought, by supplying control signal as for the emitting device.

The advantage of producing the vibrotactile feedback using the receiving device is in that the acoustic waves emitted by the emitting device are thus not disturbed by the frictions of the movable part against the inner wall of the sleeve. The radiation pattern in emission is thus stable.

On the other hand, as the receiving device receives the air waves and the acoustic waves carried by the plate, contact of the movable part against the inner walls of the sleeve (of the receiving device) either creates no disturbance or consistently very little disturbance which can easily be corrected by processing the signal, the reception signal.

Moreover, it should be noted that the invention is not limited to the embodiments described above. Indeed, it would be obvious for those skilled in the art that various modifications may be made to the embodiments described above, in the light of the teaching disclosed herein.

In particular, the different spatial distributions from one wave to another could be spatial distributions of the phase, instead of or in addition to the spatial distributions of the amplitude. In particular, the various types of control signals described above (change of contribution of the two sources and change of the phase shift between the two sources) give rise to different spatial distributions of the phase between waves.

Moreover, the control signals may not be monochromatic, but, on the contrary, have a broad spectrum. In this way, the acoustic waves emitted (in a solid or in air, according to the embodiment) would also have a broad spectrum. In this case, the emitting device would be designed such that the spectra of the acoustic waves each have at a specific frequency at least mutually different respective spatial distributions of the amplitude or phase. For example, the spatial distributions change for all frequencies, from one acoustic wave to another.

In the claims hereinafter, the terms used should not be interpreted as limiting the claims to the embodiments disclosed in the present description, but should be interpreted to include all the equivalents intended to be covered by the claims due to the wording thereof and which may be envisaged by those skilled in the art by applying their general knowledge to the implementation of the teaching disclosed herein.

The invention claimed is:

1. A system for detecting and locating a disturbance in a medium, the system comprising:
    an emitter configured to emit a plurality of successive acoustic waves in the medium, wherein each of said plurality of successive acoustic waves propagates by varying in the medium according to a specific spatial distribution of an amplitude or phase of its frequency spectrum at least at a specific frequency of said frequency spectrum;
    a receiver configured to receive the plurality of successive acoustic waves after propagation thereof in the medium, and configured to supply a reception signal based on the plurality of successive acoustic waves received; and
    a processor configured to detect and locate the disturbance in the medium on the basis of the reception signal,
    wherein the emitter is configured such that the successive spatial distributions of the amplitudes or phases of the frequency spectra of the respective successive acoustic waves are mutually different and not proportional.

2. The system according to claim 1, wherein:
    the medium comprises a plate having a contact surface;
    the acoustic waves are seismic acoustic waves propagated in the plate; and
    the disturbance is a contact on the contact surface.

3. The system according to claim 1, wherein:
    the medium comprises a fluid on a surface of a plate;
    the acoustic waves are compression acoustic waves propagated in fluid on the surface of the plate; and
    the disturbance is presence of an interruption in impedance on the plate surface, or caused by presence of an obstacle.

4. The system according to claim 3, wherein the emitter includes an emitting device comprising a piezoelectric element, piezoelectric element comprises a sleeve for emitting the compression acoustic waves.

5. The system according to claim 1, wherein the emitter includes
    an emitting device comprising first and second acoustic wave sources respectively having first and second radiation patterns, the first and second radiation patterns being concentric and different to each other, wherein
    the emitter is further configured to modify relative weighting of the amplitudes of the acoustic waves of the first and second sources, the successive weightings corresponding to the successive spatial distributions, respectively.

6. The system according to claim 5, wherein each of the first and second radiation patterns has an axis in the direction whereof it is zero, an angle formed between the axis of the first radiation pattern and the axis of the second radiation pattern being different from zero.

7. The system according to claim 5, wherein:
    each acoustic wave source comprises two piezoelectric transducing elements; and
    the emitter is further configured to polarize the two piezoelectric transducing elements having two mutually opposite potentials, respectively.

8. The system according to claim 7, wherein the emitting device comprises a piezoelectric element coupled with the medium and four electrodes covering a respective quarter of one face of the piezoelectric element, the two transducing elements of the first source comprising two mutually opposite electrodes, respectively, and the two transducing elements of the second source comprising the two other mutually opposite electrodes, respectively.

9. A method for detecting and locating a disturbance in a medium, the method comprising:
    supplying control signals to an emitting device for emitting acoustic waves, so that the emitting device emits a plurality of successive acoustic waves in the medium, wherein each of said plurality of successive acoustic waves propagates by varying in the medium according to a specific spatial distribution of an amplitude or phase of its frequency spectrum at least at a specific frequency of said frequency spectrum;
    receiving a reception signal from a device for receiving acoustic waves, receiving the plurality of successive acoustic waves after propagation thereof in the medium; and
    detecting and locating the disturbance in the medium on the basis of the reception signal;
    wherein the control signals are configured such that the successive spatial distributions of the amplitudes or phases of the frequency spectra of the respective successive acoustic waves are mutually different and not proportional.

10. The method for detecting and locating a disturbance in a medium according to claim 9, wherein:

the control signals are supplied intermittently such that mean exposure output, even in the ultrasonic range, remains below 85 dB, with a reference of $2 \cdot 10^{-5}$ Pa, in air one centimeter from the device for emitting acoustic waves;

the control signals have a specific excitation frequency band; and the method further comprises, before detecting and locating the disturbance in the medium on the basis of the reception signal:

amplifying the reception signal and converting the reception signal by an analog-digital converter, the amplification being configured such that amplitude of the received signal in absence of disturbance reaches full quantification scale of the analog-digital converter; and performing band-pass filtering of the reception signal, on a frequency band corresponding to the excitation frequency band.

11. A non-transitory computer readable medium including computer-executable instructions, wherein the instructions, when executed by a computer, cause the computer to perform the method for detecting and locating a disturbance in a medium according to claim 9.

12. A device for detecting and locating a disturbance in a medium, the device comprising:

circuitry configured to supply control to an emitting device for emitting acoustic waves, so that the emitting device emits a plurality of successive acoustic waves in the medium, wherein each of said plurality of successive acoustic waves propagates by varying in the medium according to a specific spatial distribution of an amplitude or phase of its frequency spectrum at least at a specific frequency of said frequency spectrum, receive a reception signal from a receiving device that receives the plurality of successive acoustic waves after propagation thereof in the medium, and detect and locate the disturbance in the medium on the basis of the reception signal, wherein the circuitry configures the control signals such that the successive spatial distributions of the amplitudes or phases of the frequency spectra of the respective successive acoustic waves are mutually different and not proportional.

* * * * *